United States Patent [19]

Wheeler

[11] Patent Number: 4,631,339
[45] Date of Patent: Dec. 23, 1986

[54] 1,3,5-TRIAZEPINONES

[75] Inventor: William J. Wheeler, Indianapolis, Ind.

[73] Assignee: Eli Lilly and Company, Indianapolis, Ind.

[21] Appl. No.: 701,060

[22] Filed: Feb. 13, 1985

Related U.S. Application Data

[62] Division of Ser. No. 486,132, Apr. 18, 1983, Pat. No. 4,514,564.

[51] Int. Cl.$^4$ ............................................ C07D 255/02
[52] U.S. Cl. ...................................... 540/492; 344/25
[58] Field of Search ............................... 260/239.3 R

[56] References Cited

U.S. PATENT DOCUMENTS 3,499,893  3/1970  Crast, Jr. ............................. 260/243
4,238,388  12/1980  Cantatore et al. ............ 260/239.3 R

OTHER PUBLICATIONS

M. Misiek, L. B. Crast et al., Structure-Activity Relationships etc., *Antimicrob. Ag. Chemother.*, 1, p. 54 (1972).

*Primary Examiner*—Robert T. Bond
*Attorney, Agent, or Firm*—Paul C. Steinhardt

[57] ABSTRACT

7β-[2'-triazepinone-2'-(oximine ether) acetamido] cephalosporin antibiotics are claimed. Also claimed are the 2'-triazepinone-2'-(oxime ether) acetic acid intermediates and the esters, salts and halides thereof.

7 Claims, No Drawings

1,3,5-TRIAZEPINONES

This application is a division of U.S. Pat. No. 4,514,564 issued Apr. 30, 1985.

SUMMARY

This invention relates to 3-substituted cephalosporins having a 7β-[2'-(1",3",5"-triazepin-4"-one)-2'-(oxime ether)-acetamido] group, which have the formula

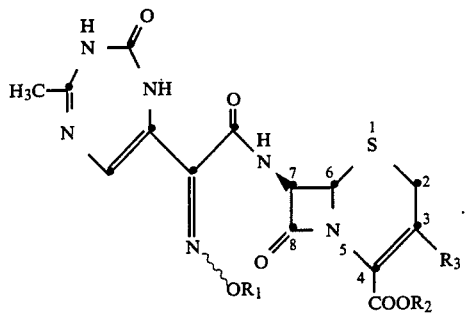

This invention also relates to intermediates in the synthesis of the above cephalosporin antibiotics, specifically the 2'-(1",3",5"-triazepin-4"-one)-2'-(oxime ether) acetic acid intermediates, and the salts, esters and acid chlorides and bromides thereof, represented by the following general formula

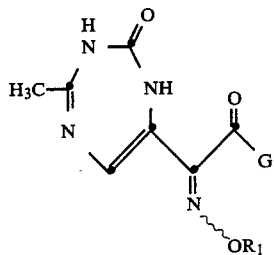

DETAILED DESCRIPTION OF THE INVENTION

This invention is directed to cephalosporin compounds of the following general formula I

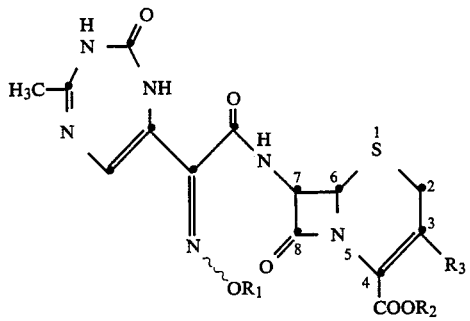

and will be referred to in the instant application as the "triazepinone cephalosporin" compounds.

This invention is also directed to an intermediate used in the synthesis of the above cephalosporin compounds. The intermediate compound has the general formula

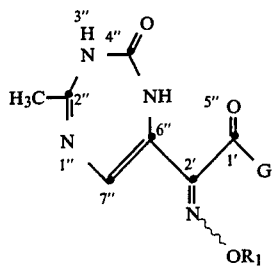

and will be referred to in the instant application as the "triazepinone oxime side chain".

In the formulas contained in this application, the mark "◄" indicates the β-configuration and the hash line "||||" indicates the α-configuration. Also, in the formulas contained in this application the geometrical isomer of the oxime ether function indicated by the following partial formula

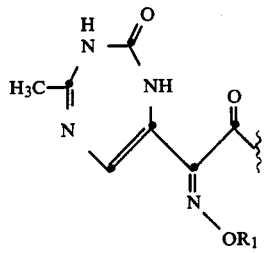

is referred to as the "Z" or "syn" isomer, while the opposite isomer, represented by the following partial formula

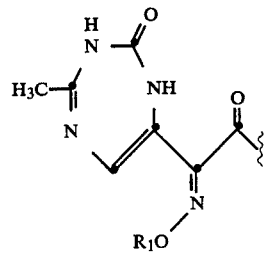

is referred to as the "E" or "anti" isomer.

It will be understood that since the triazepinone cephalosporins and the triazepinone oxime side chain intermediates of this invention are geometrical isomers of the oxime ether group, some admixture between the Z isomer and the corresponding E isomer may occur.

The triazepinone cephalosporin compounds of this invention are represented by the following general formula I

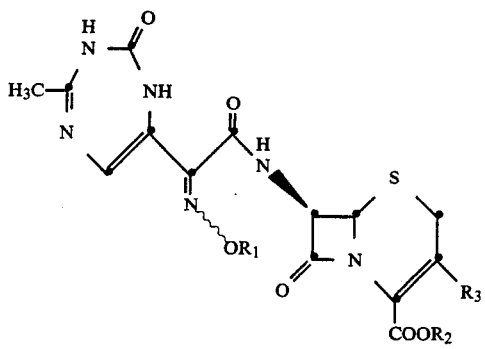

wherein:

R₁ is $C_1$ to $C_4$ alkyl, an amido-substituted alkyl, a carboxy-substituted alkyl, a carboxy-substituted cycloalkyl or an amido-substituted cycloalkyl group represented by the formula

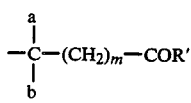

wherein m is 0 to 3, a and b when taken separately are independently hydrogen or $C_1$ to $C_3$ alkyl, or when taken together with the carbon to which they are attached form a $C_3$ to $C_7$ carbocyclic ring; R' is hydroxy, amino, $C_1$ to $C_4$ alkoxy, or —OR'', where R'' is a carboxy protecting group;

R₂ is hydrogen, a carboxy protecting group or a pharmaceutically acceptable, non-toxic salt thereof, the hydrates of said salt, or the non-toxic metabolically labile esters thereof, provided that when R₃ is hydroxy, R₂ is other than hydrogen;

R₃ is (a) hydrogen, fluoro, bromo, chloro, hydroxy, methyl, methoxy or hydroxymethyl; or (b) ($C_2$ to $C_4$ acyloxy)methyl; or (c) a methyl carbamate group of the formula

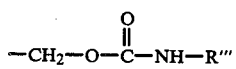

wherein R''' is hydrogen or $C_1$ to $C_4$ alkyl;

(d) a pyridinium methyl group of the formula

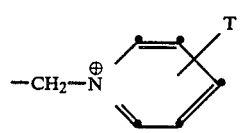

wherein T is (i) hydrogen, trifluoromethyl, $C_1$ to $C_4$ alkyl, $C_1$ to $C_4$ alkoxy, hydroxy, cyano, halo or hydroxymethyl; or (ii) carboxy, $C_1$-$C_4$ alkoxycarbonyl, $C_1$ to $C_4$ alkanoyl or $C_1$ to $C_4$ alkanoyloxy; or (iii) an amido group of the formula

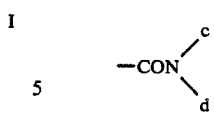

wherein c is hydrogen, methyl, ethyl or cyclopropyl and d is hydrogen, methyl or ethyl; or (iv) a group of the formula

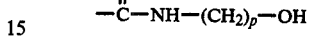

wherein p is 1 to 4; provided that (a) when the pyridinium ring is substituted with the above substituents in (iv), the pyridinium ring is additionally substituted with R₄, wherein R₄ is hydrogen or $C_1$ to $C_4$ alkyl; and (b) when T is hydroxy or halo, T is only bonded to the 3 position of the pyridinium ring; or (e) a heterocyclic thiomethyl group of the formula —CH₂—S—Y, wherein Y is

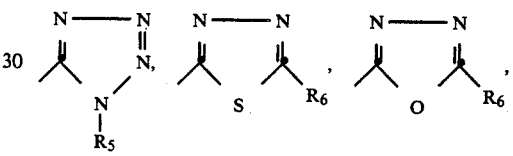

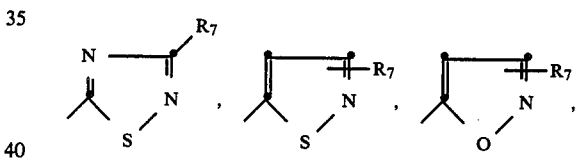

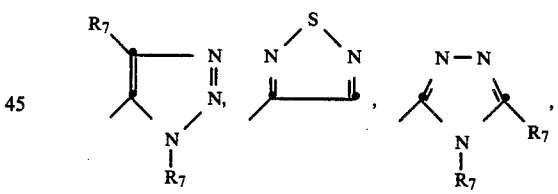

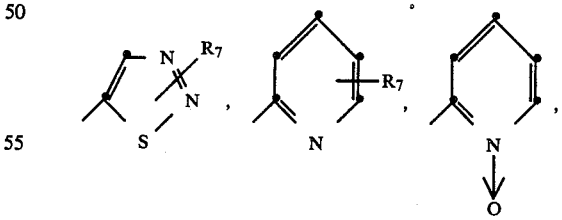

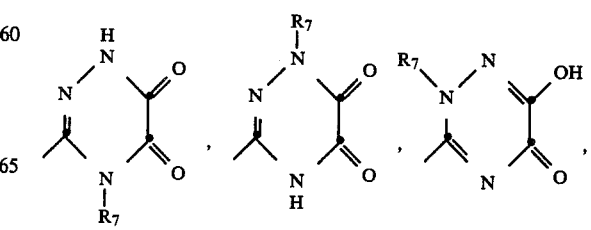

-continued

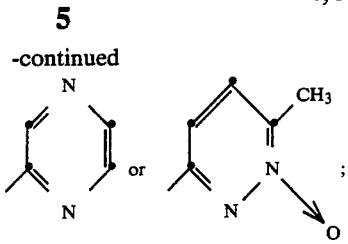

wherein
$R_5$ is hydrogen, $C_1$ to $C_4$ alkyl, —$CH_2COOH$ or —$CH_2SO_3H$;
$R_6$ is hydrogen, $C_1$ to $C_4$ alkyl, phenyl or amino; and
$R_7$ is hydrogen or $C_1$ to $C_4$ alkyl.

In the foregoing definitions of the triazapinone cephalosporin compounds, the term "$C_1$ to $C_4$ alkyl" means methyl, ethyl, propyl, iso-propyl, butyl, sec-butyl or tert-butyl.

The term "$C_1$ to $C_3$ alkyl" means methyl, ethyl, propyl or iso-propyl.

The term "$C_1$ to $C_4$ alkoxy" refers to methoxy, ethoxy, n-propoxy, iso-propoxy, sec-butoxy, n-butoxy and the like.

With respect to the term $R_1$ in formula I, the carboxy-substituted alkyl group (R' is hydroxy) represented by the formula

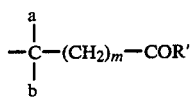

is illustrated by carboxymethyl, 2-carboxyethyl, 1-carboxyethyl, 1-carboxy-1-methylethyl, 3-carboxypropyl, 2-carboxypropyl, 4-carboxybutyl, 3-carboxypentyl, 4-carboxyheptyl, 2-carboxybutyl, and the like. When a and b are taken together, examples of the carboxy-substituted cycloalkyl groups are 1-carboxycycloprop-1-yl, 1-carboxycyclobut-1-yl, 1-carboxymethylcyclobut-1-yl, 1-carboxycyclopent-1-yl, 1-carboxycyclohex- 1-yl, 1-carboxycyclohep-1-yl, 1-carboxyethylcyclopent-1-yl, 1-carboxypropylcyclohex-1-yl, and the like. Examples of amido-substituted alkyl groups (R' is amino) are aminocarbonylmethyl, 2-aminocarbonylethyl, 3-aminocarbonylpropyl and 2-aminocarbonylprop-2-yl, and examples of the amido-substituted cycloalkyl groups are 1-aminocarbonylcycloprop-1-yl, 1-aminocarbonylcyclohex-1-yl, and like carboxamido substituted alkyl and cycloalkyl groups.

Examples of such groups when R' is $C_1$ to $C_4$ alkoxy are ethoxycarbonylmethyl, methoxycarbonylpropyl, 2-ethoxycarbonylprop-2-yl, 4-butyloxycarbonylmethyl, 3-ethoxycarbonylpropyl, 1-ethoxycarbonylcyclobut-1-yl, 1-(methoxycarbonylmethyl)cyclopent-1-yl, and like groups.

It will be appreciated by those skilled in the art that when a and b in the above formula represent different $C_1$ to $C_3$ alkyl groups, the carbon atom to which they are attached comprise a center of asymmetry. Such compounds are diastereometric and the present invention embraces individual diastereomers of these compounds as well as mixtures thereof.

The term "carboxy protecting group" indicates a carboxy group which has been esterified with one of the more commonly used carboxylic acid protecting ester groups employed to block or protect the carboxylic acid functionality while reactions involving other functional sites of the compound are carried out. Such carboxy protecting groups may be subsequently removed by any of the appropriate methods disclosed in the literature, for example acid or base catalyzed hydrolysis, hydrogenolysis, and enzymatically catalyzed hydrolysis, to yield the free carboxylic acid. Examples of such carboxylic acid group include 2-iodoethyl, tert-butyl, 2,2,2-trichloroethyl, 4-methoxybenzyl, 4-nitrobenzyl, diphenylmethyl, allyl, 4-methoxydiphenylmethyl, 4,4'-dimethoxydiphenylmethyl, benzyl, trialkylsilyl, 2,4,6-trimethoxybenzyl, trityl, 4methoxytrityl, 4,4'-dimethoxytrityl, 4,4',4"-trimethoxytrityl and like ester forming moieties. The nature of such ester forming groups is not critical so long as the ester formed therewith is stable under the reaction conditions of a reaction on another position of the molecule.

In the above definition, the term "carboxy protecting group" is not exhaustively defined. The function of such groups is to protect the reactive functional groups during the preparation of the desired products and then be removed without disrupting the remainder of the molecule. Many such protecting groups are well known in the art and the use of other groups equally applicable to the synthesis of the compounds of the present invention, such as those described in Ch. 5 of J. F. W. McOmie, "Protective Groups in Organic Chemistry", Plenum Press, 1973, will be recognized as suitable. Thus, there is no novelty or inventiveness asserted with regard to the "carboxy protecting groups" described in this specification.

The term "pharmaceutically acceptable, nontoxic salt", refers to the inorganic salts of the above compounds formed with the alkali and alkaline earth metals such as lithium, sodium, potassium, and calcium, organic base salts such as ammonium, dibenzylammonium, benzylammonium, 2-hydroxyethylammonium, bis(2-hydroxyethyl)ammonium, phenylethylbenzylamine, dibenzylethylenediamine, and like salts. Other amine salts can be formed with procaine, quinine and N-methylglusoamine, plus salts formed with basic amino acids such as glycine, ornithine, histidine, phenylglycine, lysine and arginine. These salts are useful in preparing suitable pharmaceutical compositions of the instant compounds for therapeutic purposes. In addition, when $R_3$ is a group of the formula

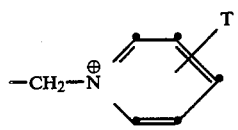

the $R_2$ group will be a carboxy anion, in other words, the molecules will exist in the pharmaceutically acceptable zwitterion form.

The hydrates of the above salts are also encompassed by the scope of the instant invention.

The term "non-toxic metabolically labile esters" refers to those biologically active ester forms which conduce, for example, to increase the blood levels and prolong the efficacy of such ester compounds. Such ester groups include lower alkoxymethyl groups, e.g. methoxymethyl, ethoxymethyl, isopropoxymethyl, α-methoxyethyl, groups such as α-lower alkoxy ($C_1$ to $C_4$) ethyl; e.g. methoxyethyl, ethoxyethyl, propoxyethyl, iso-propoxyethyl, etc; $C_1$ to $C_3$ alkylthiomethyl groups, e.g. methylthiomethyl, ethylthiomethyl, isopropylthiomethyl, etc; acyloxymethyl groups, e.g. pivaloyloxymethyl, α-acetoxymethyl, etc; ethoxycarbonyl-1-methyl; or α-acyloxy-α-substituted methyl groups, e.g. α-acetoxyethyl.

When R₃ is "C₂ to C₄ acyloxymethyl" we mean organic moieties such as acetoxymethyl, propionyloxymethyl and butyryloxymethyl.

Examples of the methyl carbamate group of R₃ include carbamoyloxymethyl, N-methylcarbamoyloxymethyl, N-butylcarbamoyloxymethyl, N-propylcarbamoyloxymethyl, N-(iso-propyl)carbamoyloxymethyl, N-butylcarbamoyloxymethyl, N-(sec-butyl)carbamoyloxymethyl and N-(tert-butyl)carbamoyloxymethyl.

When, in the Formula I, R₃ is a pyridinium group, the terms represented by "T" are exemplified as follows:

The term "C₁ to C₄ alkoxycarbonyl" refers to the methyl, ethyl, propyl, iso-propyl, butyl, sec-butyl and tert-butyl esters of a carboxylic acid, which acid is in turn bound through the carbonyl group to a pyridinium ring. Analogously, the term "C₁ to C₄ alkanoyl" refers to the formyl, acetyl, propionyl, iso-propionyl, butyryl, sec-butyryl and the tert-butyryl groups, which are bound through the carbonyl group to a pyridinium ring. Finally, the term "C₁ to C₄ alkanoyloxy" refers to the formyloxy, acetyloxy, propionyloxy, iso-propionyloxy, butyryloxy, sec-butyryloxy and tert-butyryloxy groups that are bound through the sp³ hybridized oxygen to the pyridinium ring.

By the term "halo" we mean fluoro, chloro, bromo or iodo.

The instant invention embraces compounds where the pyridinium group at R₃ is monosubstituted at ring positions 2 through 6 with any of the substituents named hereinabove, provided that, when T is halo or hydroxy, T is bonded only to the 3 position of the pyridinium ring. Examples of pyridinium groups that are in turn bound to a 3'-methylene moiety at R₃ include: pyridinium, 4-trifluoromethylpyridinium, 3-trifluoromethylpyridinium, 2-methylpyridinium, 4-methylpyridinium, 3-ethylpyridinium, 4-propylpyridinium, 4-butylpyridinium, 3-methoxypyridinium, 4-methoxypyridinium, 2-methoxypyridinium, 4-ethoxypyridinium, 3-ethoxypyridinium, 4-iso-propoxypyridinium, 3-sec-butoxypyridinium, 4-butoxypyridinium, 3-hydroxypyridinium, 4-cyanopyridinium, 3-cyanopyridinium, 3-chloropyridinium, 3-iodopyridinium, 4-(hydroxymethyl)pyridinium, 3-(hydroxymethyl)pyridinium, 4-carboxypyridinium, 4-carbomethoxypyridinium, 3-carbomethoxypyridinium, 2-carbomethoxypyridinium, 4-carboethoxypyridinium, 3-carbopropoxypyridinium, 4-carbobutoxypyridinium, 4-formylpyridinium, 2-formylpyridinium, 3-formylpyridinium, 4-acetylpyridinium, 3-acetylpyridinium, 4-propionylpyridinium, 4-tert-butyrylpyridinium, 3-butyrylpyridinium, 3-formyloxypyridinium, and 3-iso-propionyloxypyridinium.

It should be noted that the amido substituent of the pyridinium methyl group, represented by the formula

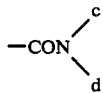

may be substituted, monosubstituted or disubstituted, as defined, and, in the disubstituted embodiments, the N-substituents may be the same or different. Examples of amido-substituted pyridinium rings include N-methyl pyridinium-4-carboxamide, pyridinium-3-carboxamide, pyridinium-4-carboxamide, N-cyclopropyl pyridinium-3-carboxamide, N-methyl-N-ethyl pyridinium-3-carboxamide, N,N-dimethylpyridinium-3-carboxamide, N-ethyl pyridinium-4-carboxamide and the like.

Examples of a pyridinium group substituted with a group of the formula

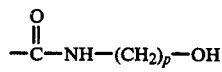

include N-(hydroxymethyl) pyridinium-3-carboxamido, N-(hydroxymethyl) pyridinium-4-carboxamido, N-(hydroxyethyl) pyridinium-3-carboxamido, N-(hydroxypropyl) pyridinium-4-carboxamido, N-(hydroxybutyl) pyridinium-3-carboxamido and the like. The preferred amido substituted pyridiniums are the N-(hydroxymethyl) pyridinium-3-carboxamido and the N-(hydroxymethyl) pyridinium-4-carboxamido.

The preferred pyridinium methyl groups are the unsubstituted pyridinium methyl group and the (4-carboxamido)pyridinium methyl group.

Examples of heterocyclic groups Y when, in Formula I, R₃ is a heterocyclic thiomethyl group of the formula —CH₂—S—Y, are 1H-tetrazol-5-yl, 1-methyl-1H-tetrazol-5-yl, 1-(n-propyl)-1H-tetrazol-5-yl, 1-(sec-butyl)-1H-tetrazol-5-yl, 1-(2-acetic acid)-1H-tetrazol-5-yl, 1-(methylsulfonic acid)-1H-tetrazol-5-yl, 5-amino-1,3,4-thiadiazol-2-yl, 5-phenyl-1,3,4-thiadiazol-2-yl, 5-methyl-1,3,4-thiadiazol-2-yl, 5-ethyl-1,3,4-thiadiazol-2-yl, 5-(n-butyl)-1,3,4-thiadiazol-2-yl, 1,3,4-oxadiazol-2-yl, 5-phenyl-1,3,4-oxadiazol-2-yl, 5-amino-1,3,4-oxadiazol-2-yl, 5-methyl-1,3,4-oxadiazol-2-yl, 5-(iso-propyl)-1,3,4-oxadiazol-2-yl, 5-(tert-butyl)-1,3,4-oxadiazol-2-yl, 1,2,4-thiadiazol-2-yl, 3-methyl-1,2,4-thiadiazol-5-yl, 3-ethyl-1,2,4-thiadiazol-5-yl, 3-(n-butyl)-1,2,4-thiadiazol-5-yl, isothiazol-5-yl, 3-methylisothiazol-5-yl, 4-methyl-isothiazol-5-yl, 3-ethylisothiazol-5-yl, 4-(n-propyl)-isothiazol-5-yl, 3-(iso-propyl)-isothiazol-5-yl, 4-(n-butyl)-isothiazol-5-yl, 3-(sec-butyl)-isothiazol-5-yl, isoxazol-5-yl, 3-methyl-isoxazol-5-yl, 4-methyl-isoxazol-5-yl, 3-ethyl-isoxazol-5-yl, 4-ethyl-isoxazol-5-yl, 3-(n-propyl)-isoxazol-5-yl, 4-(iso-propyl)-isoxazol-5-yl, 4-(n-butyl)-isoxazol-5-yl, 3-(sec-butyl)-isoxazol-5-yl, 1H-1,2,3-triazol-5-yl, 1-methyl-1H-1,2,3-triazol-5-yl, 4-methyl-1H-1,2,3-triazol-5-yl, 1,4-dimethyl-1H-1,2,3-triazol-5-yl, 1-ethyl-1H-1,2,3-triazol-5-yl, 4-ethyl-1H-1,2,3-triazol-5-yl, 1,4-diethyl-1H-1,2,3-triazol-5-yl, 1-(n-propyl)-1H-1,2,3-triazol-5-yl, 4-(iso-propyl)-1H-1,2,3-triazol-5-yl, 1,4-(di-n-butyl)-1H-1,2,3-triazol-5-yl, 1-(sec-butyl)-1H-1,2,3-triazol-5-yl, 1,2,5-thiadiazol-3-yl, 1,3,4-triazol-5-yl, 1-methyl-1,3,4-triazol-5-yl, 1-ethyl-1,3,4-triazol-5-yl, 1-(n-butyl)-1,3,4-triazol-5-yl, 2-methyl-1,3,4-triazol-5-yl, 2-ethyl-1,3,4-triazol-5-yl, 2-propyl-1,3,4-triazol-5-yl, 1,2-dimethyl-1,3,4-triazol-5-yl, 1,2-(di-n-butyl)-1,3,4-triazol-5-yl, 1-methyl-2-ethyl-1,3,4-triazol-5-yl, 1-ethyl-2-methyl-1,3,4-triazol-5-yl, 1-propyl-2-methyl-1,3,4-triazol-5-yl, 1,2,3-thiadiazol-5-yl, 4-methyl-1,3,4-thiadiazol-5-yl, 4-ethyl-1,2,3-thiadiazol-5-yl, 4-propyl-1,2,3-thiadiazol-5-yl, 4-butyl-1,2,3-thiadiazol-5-yl, pyridin-6-yl, 2-methylpyridin-6-yl, 3-methylpyridin-6-yl, 4-methylpyridin-6-yl, 5-methylpyridin-6-yl, 2-ethylpyridin-6-yl, 4-ethylpyridin-6-yl, 3-ethylpyridin-6-yl, 2-(n-propyl)pyridin-6-yl, 3-(n-propyl)pyridin-6-yl, 4-(iso-propyl)pyridin-6-yl, 2-(n-butyl)pyridin-6-yl, 4-(sec-butyl)pyridin-6-yl, pyridin- 6-yl-N-oxide, 1,6,4,5-tetrahydro-5,6-dioxo-4-methyl-as-triazin-3-yl, 1,6,4,5-tetrahydro-5,6-dioxo-as-triazin-3-yl, 1,6,4,5-tetrahydro-5,6-dioxo-4-ethyl-as-triazin-3-yl, 1,6,4,5-tetrahydro-5,6-dioxo-4-(n-propyl)-as-triazin-3-yl, 1,6,4,5-tetrahydro-5,6-dioxo-4-(n-butyl)-as-triazin-3-yl, 1,6,4,5-tetrahydro-5,6-dioxo-1-methyl-as-triazin-3-yl, 1,6,4,5-tetrahydro-5,6-dioxo-1-ethyl-as-triazin-3-yl, 1,6,4,5-tetrahydro-5,6-dioxo-1-(iso-propyl)-as-triazin-3-yl, 1,6,4,5-tetrahydro-5,6-dioxo-1-(n-butyl)-as-triazin-3-yl, 2,5-dihydro-5-oxo-6-hydroxy-as-triazin-3-yl, 2,5-dihydro-5-oxo-6-hydroxy-2-methyl-as-triazin-3-yl, 2,5-dihydro-5-oxo-6-hydroxy-2-ethyl-as-triazin-3-yl, 2,5-dihydro-5-oxo-6-hydroxy-(2-n-propyl)-as-triazin-3-yl, 2,5-dihydro-5-oxo-6-hydroxy-(2-n-butyl)-as-triazin-3-yl, pyrazin-2-yl, 3-methyl-2-(N-oxide)-pyridizin-6-yl, and like heterocycles.

Preferred heterocycles are 1H-1,2,3-triazol-5-yl, 1-methyl-1H-tetrazol-5-yl, 1-(2-acetic acid)-1H-tetrazol-5-yl, 1-(methylsulfonic acid)-1H-tetrazol-5-yl, 5-methyl-1,3,4-thiadiazol-2-yl, 2,5-dihydro-5-oxo-6-hydroxy-2-methyl-as-triazin-3-yl and 1,6,4,5-tetrahydro-5,6-dioxo-4-methyl-as-triazin-3-yl.

Finally, a proviso in the description of the above cephalosporin is that when $R_3$ is hydroxy, $R_2$ is other than hydrogen.

The intermediate triazepinone oxime side compound of this invention has the following general formula

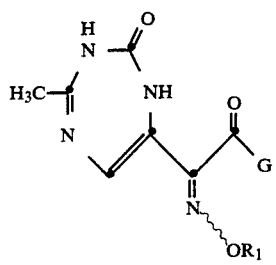

wherein $R_1$ has the same meaning as defined for Formula I; G is chloro, bromo, hydroxy, $C_1$ to $C_4$ alkoxy, phenoxy or the residue of a group forming an activated ester; or a group of the formula

wherein $M^\oplus$ is a monovalent cation.

The term "$C_1$ to $C_4$ alkoxy" has the same meaning as defined for Formula I.

The term "active ester" used in the above Formula II refers to the group G where G is p-nitrophenoxy, 2,4-dinitrophenoxy, pentachlorophenoxy, molecules of the formula

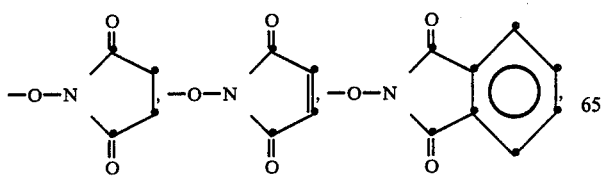

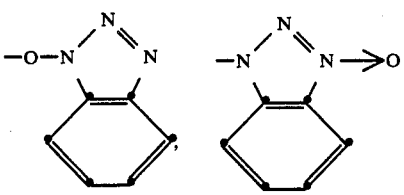

and the like. The term "active ester" also includes acid anhydrides and mixed acid anhydrides (i.e., where G is

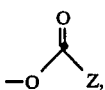

and Z is a substituent bound to the carbonyl through a carbon or an oxygen).

The mixed acid anhydride is exemplified by the mixed anhydrides with carbonic acid monoesters, such as methyl carbonate, isobutyl carbonate, etc. and the mixed anhydrides with lower alkanoic acids which may optionally be substituted by halogen, such as pivalic acid, trichloroacetic acid, etc. The preferred active ester group is the isobutylcarbonate group, that is, where G is

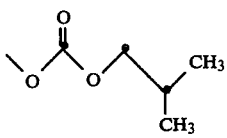

By the term "monovalent cation" we mean cations such as the lithium, sodium and potassium cations, and the like, and the ammonium cations such as ammonium, dibenzylammonium, benzylammonium, phenylethylbenzylammonium, 2-hydroxyethylammonium, dicyclohexylammonium, and the like.

The preferred method of synthesis for the compounds of Formula I of the instant application involves acylating a compound of the Formula III

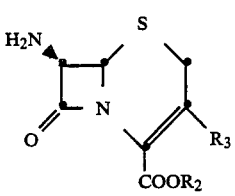

with the intermediate triazepinone oxime side chain of Formula II

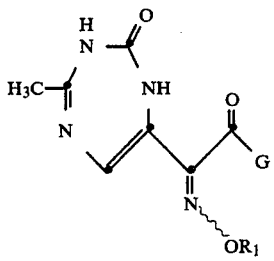

wherein $R_1$, $R_2$, $R_3$ and G have the same meanings as described before.

In this preferred method of synthesis the desired $R_3$ group is in place before the acylation reaction is carried out.

The preferred variation for carrying out the above acylation reaction occurs when G is an active ester group. Preferred groups at G for the active ester include groups of the formula:

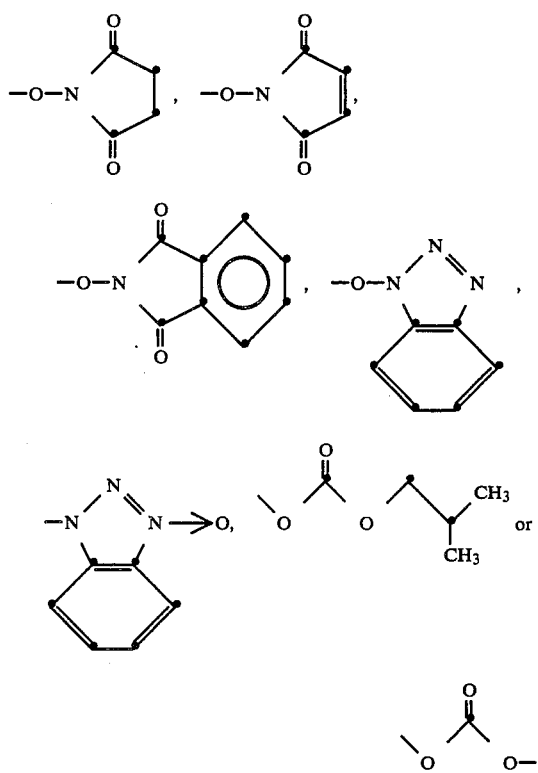

with the isobutylcarbonate residue being the most preferred.

Acylation of a compound of formula III with an intermediate triazepinone oxime side chain of formula II (wherein $R_3$ is acetoxymethyl, $R_2$ is benzhydryl, $R_1$ is methyl and G is isobutylcarbonate) is further exemplified by Example 4 in the Experimental Section.

Alternatively, when G in Formula II is hydroxy or the salt form thereof, the triazepinone oxime side chain (Formula II) is coupled with the 7-amino nucleus (Formula III) via N-acylation employing a suitable condensing agent. The condensing agent is exemplified by N,N'-disubstituted carbodiimides such as N,N'-dicyclohexylcarbodiimide, N,N'-diethylcarbodiimide, N,N'-di-(n-propyl)carbodiimide, N,N'-di(isopropylcarbodiimide, N,N'-diallylcarbodiimide, N,N'-bis(p-(dimethylamino)-phenyl)carbodiimide, N-ethyl-N'-(4"-ethylmorpholinyl)carbodiimide and the like, other suitable carbodiimides being disclosed by Sheehan in U.S. Pat. No. 2,938,892 and by Hofmann et al. U.S. Pat. No. 3,065,224; azolides such as N,N'-carbonylimidazole, N,N'-thionyldiimidazol, etc.; dehydrating agents such as N-ethoxycarbonyl-2-ethoxy-1,2-dihydroquinoline, phosphorus oxychloride, alkoxyacetylene, etc., and 2-halogenopyridinium salts (such as 2-chloropyridinium methyl iodide, 2-fluoropyridinium methyl iodide, etc.).

In addition, the above preferred method of synthesis for the cephalosporin compound in Formula I can also be carried out when G is chloro or bromo.

When G is $C_1$ to $C_4$ alkoxy or phenoxy in the above formula II, the compounds are esters which can be converted to the active esters, the carboxylic acid or carboxylate salt or the acyl chloride or bromide by methods well known in the art. The latter can be used in the acylation of the cephalosporin nucleus represented by Formula III, above.

An alternative method of synthesis of the cephalosporin compounds of Formula I, wherein $R_3$ is a pyridinium methyl group of the formula

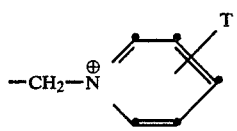

or a heterocyclic thiomethyl group of the formula

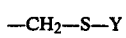

(where T and Y are as described for Formula I), entails the reaction of a 3-halomethylcephalosporin, represented by the Formula IV

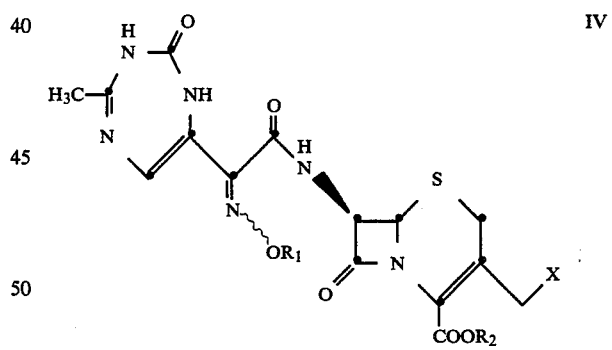

(wherein $R_1$ and $R_2$ are as defined above for Formula I and X is chloro, bromo or iodo), with a pyridine moiety of the formula

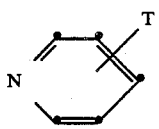

or a heterocyclic mercaptide moiety (derived from the above described heterocyclic thiol moieties, H—S—Y) of the formula

wherein M⊕ is a suitable non-nucleophilic cation such as sodium, potassium or ammonium. Preferably, X is iodo and R₂ is a trialkylsilyl group such as tri(C₁ to C₄ alkyl)silyl ester, for example, trimethylsilyl or triethylsilyl.

It is also desirable that any nucleophilic substituents on the pyridine and heterocyclic mercaptide, such as carboxy, hydroxy, and sulfonic acid functions, be suitably protected so that the substituents do not interfere with the displacement reaction involving the nitrogen of the pyridine or the sulfur of the heterocyclic mercaptide. The protecting groups can be removed after the displacement reaction is carried out.

The 3-halomethyl substituted compounds of Formula IV can be prepared by methods known in the art, for example, by the acylation of a 3-halomethyl-7-amino-3-cephem nucleus compound. The preferred 3-iodomethyl compounds of the formula IV are best obtained by the method described by R. Bonjouklian, U.S. Pat. No. 4,266,049. According to this method, a 7-acylamido-3-acetoxymethyl-3-cephem-4-carboxylic acid is first silylated to block reactive groups such as the C₄ carboxylic acid group and the silylated derivative is reacted with a trialkylsilyliodide, e.g. trimethylsilyliodide (TMSI), to form the 3-iodomethyl silylated derivative. The latter is then reacted with the above pyridine or the above heterocyclic mercaptide and the silyl blocks are hydrolyzed to provide a compound of the Formula I. The preparation of the triazepinone cephalosporin compounds (Formula 1) by this method is illustrated by the following general reaction Scheme I:

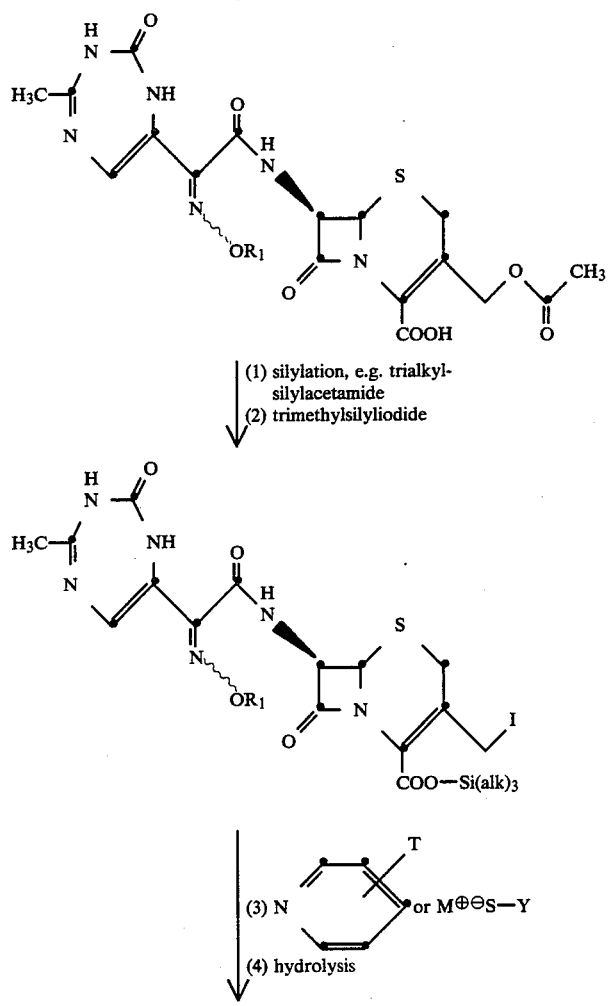

Scheme I

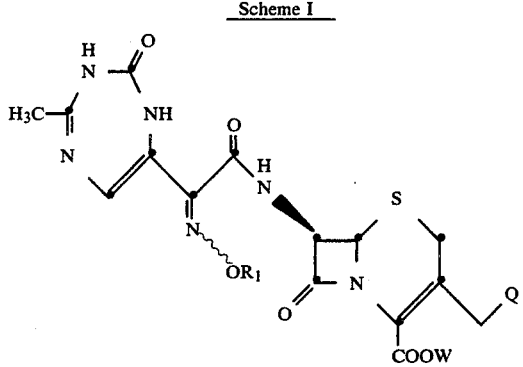

In the above Scheme, when

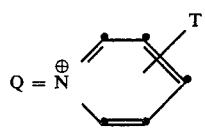

W is a negative charge, and when Q=S—Y, W is hydrogen.

The reaction is carried out with either the pyridine or the heterocyclic mercaptide at a temperature between about 20° C. and about 45° C. in an inert aprotic organic solvent under substantially anhydrous conditions. The reaction in either case is conveniently carried out at ambient temperature or at slightly elevated temperatures. Solvents which can be used with the pyridine and the mercaptide nucleophiles are, for example, acetonitrile propionitrile dimethylformamide, dimethylacetamide and like commonly used aprotic solvents.

Alternatively, the compounds of Formula I, wherein $R_3$ is a pyridinium methyl substitutent of the formula

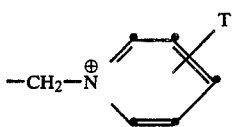

or a heterocyclic thiomethyl group of the formula

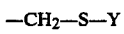

can be prepared by the well-known displacement reaction using a 3-acetoxymethyl-3-cephem-4-carboxylic acid as a substrate. The acetoxy group is displaced by a pyridine or a heterocyclic mercaptide (derived from the above-described heterocyclic thiol moiety, H—S—Y), as illustrated in the following Scheme II:

Scheme II

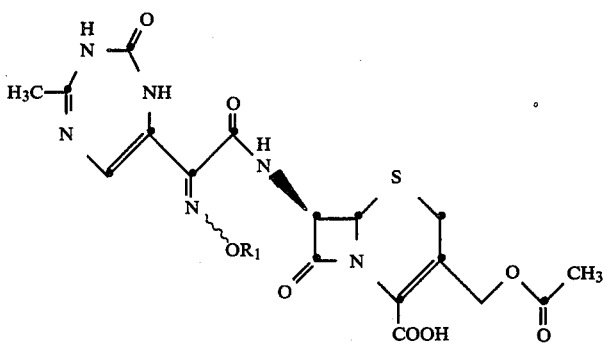

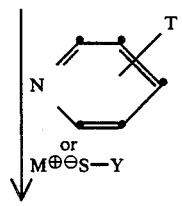

Scheme II

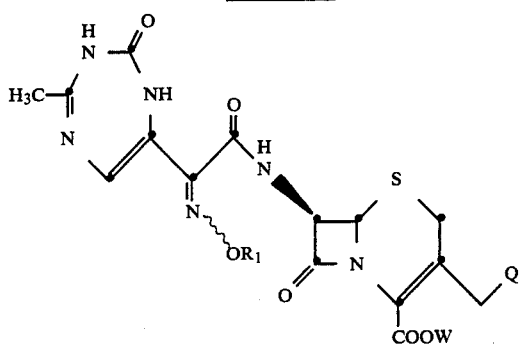

In Scheme II, $R_1$, W, Q, $M^{\oplus}$, T and Y mean the same as defined for Scheme I.

The preparation of the 3-heterocyclicthiomethyl substituted compounds (Formula I, $R_3$ is $-CH_2-S-Y$) by the displacement reaction in Scheme II is best carried out by the method of Hatfield, U.S. Pat. No. 4,144,391, issued Mar. 13, 1979. According to this method the displacement reaction is carried out under anhydrous conditions.

The preparation of 3-pyridinium methyl triazepinone cephalosporin compounds according to the method described by Scheme II is carried out in a solvent system comprising water and a water miscible solvent such as acetone or acetonitrile. In general the reaction proceeds at a temperature between about 25° C. and about 65° C.

As with Scheme I, in Scheme II, it is also desirable that nucleophilic substituents on the pyridine and heterocyclic mercaptide, such as carboxy, hydroxy and sulfonic acid functions, be suitably protected so these substituents do not interfere with the displacement reaction involving the nitrogen of the pyridine or the sulfur of the heterocyclic mercaptide. The protecting groups can be removed once the displacement reaction is carried out.

The synthesis of the intermediate triazepinone oxime side chain compound of Formula II is demonstrated generally below in Scheme III.

Scheme III

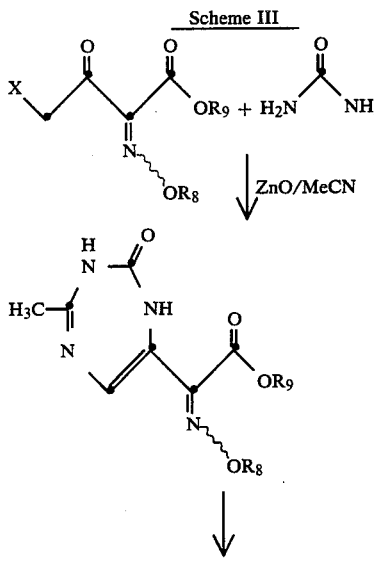

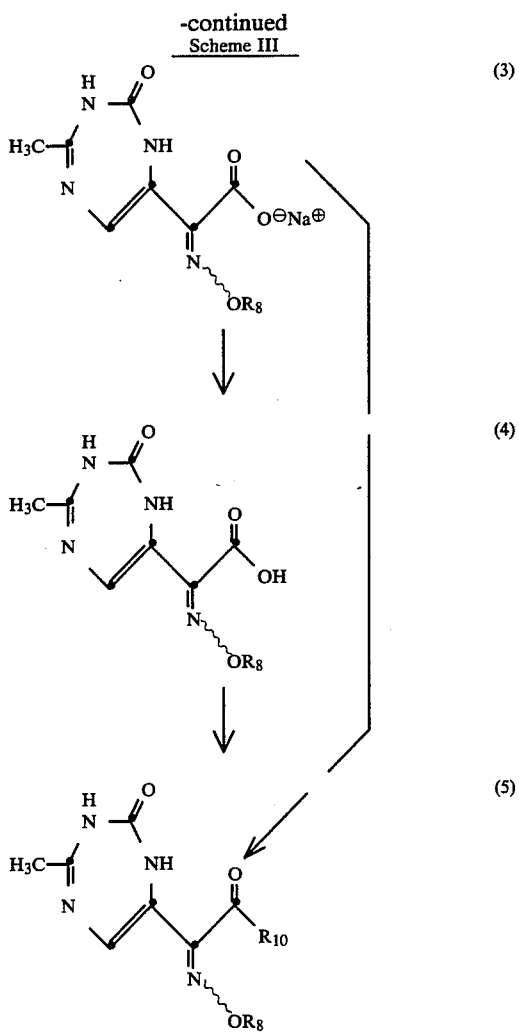

In the above Scheme III, $R_8$ is $C_1$ to $C_4$ alkyl or a group of the formula

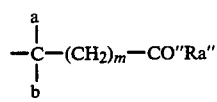

where a, b and m are the same as defined for Formula I, and "Ra" is amino, $C_1$ to $C_4$ alkoxy, or a group of the formula $-OR''$ where $R''$ is a carboxy protecting group.

$R_9$ is $C_1$ to $C_4$ alkyl or phenyl and X is chloro or bromo. Also, $R_{10}$ is $C_1$ to $C_4$ alkoxy, phenoxy, chloro, bromo or a group of the formula —O—J wherein J is the residue of a group forming an activated ester as the term "activated ester" is as defined for Formula II.

The synthesis of compound 1 of Scheme III ($\gamma$-halo-$\alpha$-(oximino ether) acetate ester) is described in Scheme IV below. Compound 2 (triazepinone oxime side chain ester) is made by heating at about reflux temperature at least about 1.1 molar equivalents of urea with about one molar equivalent of compound 1 in the presence of at least about one-half molar equivalent of zinc oxide in acetonitrile. Preferably about 5 molar equivalents of urea to about 1 molar equivalent each of zinc oxide and Compound 1 are used.

The reaction converting Compound 1 to Compound 2 is further exemplified in the Experimental Section below as Example 1.

Compound 3 of the above Scheme III (triazepinone oxime side chain carboxylic acid salt) is made by saponification of Compound 2. Suitable conditions for this reaction include the use of 5N sodium hydroxide solution at room temperature. The saponification of Compound 2 to Compound 3 is further exemplified in the Experimental Section in Example 2, below.

Compound 4 in the above Scheme III (triazepinone oxime side chain carboxy acid) is made by acidifying compound 3. Suitable conditions for this acidification include the use of 1N hydrochloric acid solution at room temperature. The acidification of Compound 3 to Compound 4 is further illustrated in the Experimental Section in Example 3, below.

Compound 5 in the above Scheme III (triazepinone oxime side chain, ester, active ester, chloride or bromide) can be made by several methods well known in the art. More specifically the Compound 5 where $R_{10}$ is chloro or bromo, can be made by reacting either Compound 4 or Compound 3 with an appropriate halogenation agent such as $SOCl_2$, $PCl_5$, $PCl_3$ for the acid chloride, and oxalyl bromide, $PBr_3$, $PBr_5$, $SOBr_2$ and $Ph_3PBr_2$ for the acid bromide.

The synthesis of Compound 5 when $R_{10}$ is $C_1$ to $C_4$ alkoxy or phenoxy can be accomplished by reacting the appropriate Compound 5 when $R_{10}$ is chloro or bromo with a $C_1$ to $C_4$ alcohol or phenol. Alternatively, the synthesis of these ester compounds can be carried out using as substrate Compound 5 when $R_{10}$ is hydroxy or salt form and the appropriate $C_1$ to $C_4$ alcohol in the presence of a condensing agent. The condensing agent is exemplified by N,N'-disubstituted carbodiimides such as N,N'-dicyclohexylcarbodiimide, N,N'-diethylcarbodiimide, N,N'-di-(n-propyl)carbodiimide, N,N'-di-(iso)propyl)carbodiimide, N,N'-diallylcarbodiimide, N,N'-bis(p-dimethylaminophenyl)carbodiimide, N-ethyl-N'-(4''-ethylmorpholinyl)carbodiimide and the like, other suitable carbodiimides being disclosed by Sheehan in U.S. Pat. No. 2,938,892 and by Hofmann et al. U.S. Pat. No. 3,065,224; azolides such as N,N'-carbonylimidazole, N,N'-thionyldiimidazole, etc.; dehydrating agents such as N-ethoxycarbonyl-2-ethoxy-1,2-dihydroquinoline, phosphorus oxychloride, alkoxyacetylene, etc., and 2-halogenopyridinium salts (such as 2-chloropyridinium methyl iodide, 2-fluoropyridinium methyl iodide, etc.).

The synthesis of Compound 5 when $R_{10}$ is a group of the formula —O—J wherein J is the residue of a group forming an activated ester can be made by methods well-known in the art. More specifically, reaction of the oxy anion of the activated group of the formula $$^{\ominus}O—J$$

with a substrate Compound 5 wherein $R_{10}$ is chloro or bromo results in the desired Compound 5 where $R_{10}$ is an activated ester group of the formula $$—O—J$$

Also, the activated ester derivatives of Compound 5 can be made from substrate Compound 5, when $R_{10}$ is the hydroxy or the salt form and the alcoholic form of the active ester-forming group of the formula $$HO—J$$

in the presence of a condensing agent. Suitable condensing agents as the same as those discussed above for the synthesis of Compound 5 wherein $R_{10}$ is $C_1$ to $C_4$ alkoxy or phenoxy.

The synthesis of Compound 5 when $R_{10}$ is a group of the formula —O—J wherein J is the residue of a group forming an activated ester is further exemplified in the Experimental Section in Example 4, Step A.

The synthesis of the starting material Compound 1 ($\gamma$-halo-$\alpha$-(oximino ether) acetate ester) in the above Scheme III is illustrated below in Scheme IV:

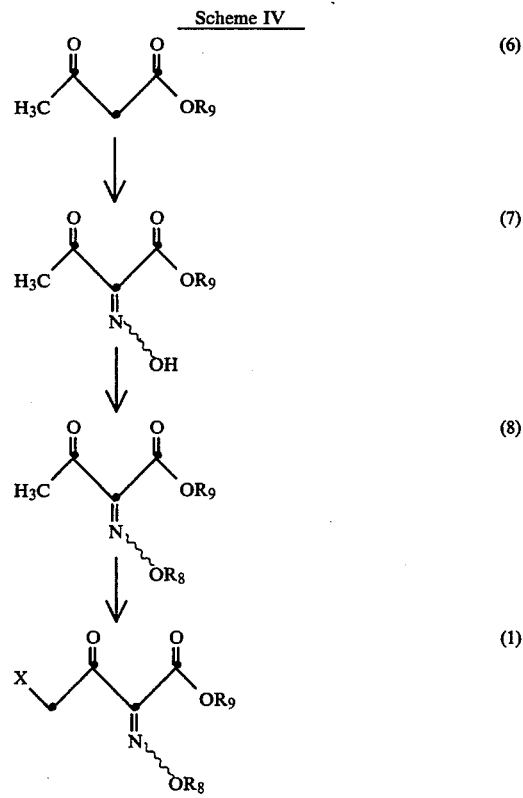

In the above Scheme IV, the terms $R_8$, $R_9$ and X are the same as defined for Scheme III.

Referring to the above Scheme IV, an ester of acetoacetate (Compound 6, commercially available) is dissolved in acetic acid and about one molar equivalent of sodium nitrite is added, while offsetting the effect of the resultant isotherm by immersing the reaction flask in a coolant such as an ice/alcohol bath. From this reaction is isolated an E, Z mixture of Compound 7 (2-(E,Z)-oxime-3-ketobutyrate ester).

Compound 8 (2-(E,Z)(substituted) alkyloximino ether-3-ketobutyrate ester) in the above Scheme IV is synthesized by alkylating the oxime group of Compound 7. Specifically, Compound 8 when $R_8$ is $C_1$ to $C_4$ alkyl is made by reacting Compound 7 with the corresponding alkyl sulfate or halide. For example, Compound 7 where $R_9$ is ethyl is reacted with methyl sulfate in acetone in the presence of potassium carbonate at 10° C. for 2 to 3 hours under a nitrogen atmosphere gives the corresponding Compound 8 wherein $R_8$ is methyl.

The Compound 8 wherein $R_8$ is a group of the formula

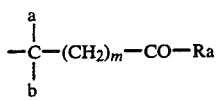

(where a, b, m and Ra are as described in $R_8$ for Scheme III), can be made by alkylating Compound 7 with a compound represented by Formula V

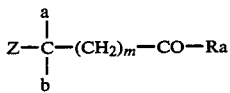

V wherein a, b, m and Ra are as described for $R_8$ and Z is chloro, bromo, iodo, sulfato or a sulfonyloxy group such as tosylate. The alkylation reaction is generally carried out in the presence of a base, e.g. potassium carbonate or sodium hydride, and is preferably conducted in an organic solvent, for example, dimethylsulfoxide, a cyclic ether such as tetrahydrofuran or dioxan, or an N,N-disubstituted amide such as dimethylformamide.

Compound 8 is converted to Compound 1 (γ-halo-α-(methoximino ether) acetate ester), the same compound as Compound 1 in Scheme III) by well-known methods of chlorination or bromination. One method comprises reacting the appropriate compound 8 with chlorine or bromine and p-toluenesulfonic acid in a suitable solvent such as methylene chloride.

The triazepinone cephalosporin compounds claimed in the instant application (represented by Formula I above), either as free carboxylic acids or as non-toxic pharmaceutically acceptable salts, the hydrates of said salts, or the non-toxic metabolically labile esters are useful for treating infections in warm-blooded animals caused by gram-positive and by gram-negative bacteria. The compounds can be administered parenterally using pharmaceutically acceptable formulations. The antibiotic compounds of the formula (wherein $R_2$ is H, or a metabolically labile ester, or the pharmaceutically acceptable, non-toxic salts thereof) can be administered in an effective dose of between about 50 mg to about 2.5 g in the treatment and control of infectious diseases. The particular dosage regime may vary depending on such factors as the nature of the infection; the severity of the disease, the general health and age of the patient as well as the tolerance of the individual patient to the antibiotic. For example, the antibiotic may be administered two or more times per day and such treatment may extend for several days to two weeks or longer if necessary. The compounds can be administered intramuscularly or intravenously. For the i.v. route the compounds can be administered by the drip method whereby a pharmaceutical formulation comprising the antibiotic and a physiologically acceptable diluent is infused. Pharmaceutically acceptable diluents include, for example, 5% dextrose, 0.9% saline, Ringer's solution or other suitable diluents.

These compounds can also be administered as veterinary compositions, such as, for example, in the feed or drinking water of farm animals to treat infections such as colibacillosis or swine dysentery.

Alternatively, these compounds can be used as surface disinfectants. Solutions containing as little as 0.1 percent by weight of the antibiotic are effective for disinfecting purposes. Such solutions, preferably also containing a detergent or other cleansing agent, are useful for disinfecting objects such as glassware, dental and surgical instruments. Solution of the antibiotic of between about 5% and about 25% can be applied to the skin to control infections associated with abrasions, cuts and the like.

The antibacterial activity of the compounds of this invention extends to such gram-positive microbes such as *Staphylococcus aureus, Staphylococcus epidermidis, Streptococcus pyogenes* and *Streptococcus pneumoniae*, and gram-negative microbes such as *Haemophilus influenzae, Shigella sonnei, Escherichia coli, Klebsiella pneumoniae, Enterobacter aerogenes,* and *Providentia rettgeri.*

EXPERIMENTAL SECTION

In the following experimental procedure, the references to "dry column silica gel column chromatography" embodies the following general procedure:

Dry column silica gel or alumina (I.C.N. Nutritional Biochemicals) is poured into a column fitted with a fritted Büchner funnel and a stopcock at one end. An additional amount of this dry column silica gel, to which the compound to be chromatographed has been adsorbed, is added to the top of the column. A paper filter disc is placed at the top of the column and the desired eluting solvent mixture is started through the column. The eluant was collected in 25 ml. fractions. The progress of the separation is followed by thin layer chromatography and the fractions are combined when appropriate.

The abbreviations v:v, h., mmol and psi stand for volume to volume, hours, millimoles, and pounds per square inch, respectively.

The abbreviations M.S. and n.m.r. stand for mass spectrum and nuclear magnetic resonance spectrum, respectively.

In conjunction with the n.m.r. spectra, the following abreviations are used: "s" is singlet, "d" is doublet, "dd" is doublet of doublets, "br. s" is broad singlet, "t" is triplet, "q" is quartet, and "m" is multiplet. "J" indicates the coupling constant in Hertz. "DMSO/d$_6$" is dimethyl sulfoxide where all protons have been replaced with deuterium.

The n.m.r. spectra were obtained on a Varian Associates EM-390 90 MHz or a Jeol FT 90Q instrument. The chemical shifts are expressed in δ values (parts per million downfield from tetramethylsilane).

EXAMPLE 1

Ethyl [2'-(4'',5''-dihydro-2''-methyl-3''-H-1'',3'',5''-triazepin-4''-oxo-6''-yl)-2-(E,Z)-methoximino] acetate.

Ethyl γ-bromo-α-methoximinoacetoacetate (25.2 g, 100 mmol), urea (30 g, 500 mmol), zinc oxide (8.1 g, 100 mmol) and acetonitrile (1 L) were combined and stirred under reflux for 48 hours. The reaction solution was allowed to cool, filtered and the acetonitrile was removed in vacuo. The residue was triturated with ethyl acetate and again filtered. The filtrate was reduced in volume, then chromatographed over neutral aluminum oxide (activity 1) using ethyl acetate as the eluant. The product-containing fractions were combined and the ethyl acetate was evaporated in vacuo. The residue was recrystallized from isopropyl alcohol to yield 2.0 g of ethyl [2'-(4'',5''-dihydro-2''-methyl-3''-H-1'',3'',5''-triazepin-4''-oxo-6''-yl)-2'-(E,Z)-methoximino] acetate: n.m.r. (CDCl$_3$) δ1.45 (t, 3, methyl of ester group), 2.3 (s, 3, 2''-methyl), 4.07 (s, 3, methoximino methyl), 4.45 (q, 2, methylene of ester group), 6.15 (br. s, 1, triazepinone ring amide), 7.55 (s, 1, 7''-proton), 9.38 (br. s, 1, triazepinone amide proton); M.S.: M+ =254.

EXAMPLE 2

Sodium [2'-(4'',5''-dihydro-2''-methyl-3''-H1'',3'',5''-triazepin-4''-oxo-6''-yl)-2'-(E,Z)-methoximino acetate To a solution of ethyl [2'-(4'',5''-dihydro-2''-methyl-3''-H-1'',3'',5''-triazepin-4''-oxo-6''-yl)-2'-(E,Z)-methoximino] acetate (0.508 g, 2 mmol) in ethanol (2B, 10 ml) was added 5N sodium hydroxide solution (0.44 ml, 2.2 mmol) with stirring at room temperature. Precipitation of a white solid occurred approximately 5 minutes after solution was affected. The suspension was stirred at room temperature for 1.75 hours. The resultant precipitate was collected by filtration, washed with ethanol and dried under vacuum to yield 0.454 g of sodium [2'-(4'',5''-dihydro-2''-methyl- 3''-H-1'',3'',5''-triazepin-4''-oxo-6''-yl)-2'-(E,Z)-methoximino] acetate.

EXAMPLE 3

2'-(4'',5''-Dihydro-2''-methyl-3''-H-1'',3'',5''-triazepin-4''-oxo-6''-yl)-2'-(E,Z)-methoximino acetic acid Sodium [2'-(4'',5''-dihydro-2''-methyl-3''-H-1'',3'',5''-triazepin-4''-oxo-6''-yl)-2'-(E,Z)-methoximino] acetate (0.454 g) was dissolved in water and the pH of the solution was adjusted to 2 by the addition of 1N hydrochloric acid. The resultant crystals were collected by filtration, then dried in vacuo to yield 0.263 g of 2'-(4'',5''-dihydro-2''-methyl-3''-H-1'',3'',5''-triazepin-4''-oxo-6''-yl)-2'-(E,Z)-methoximino acetic acid.

EXAMPLE 4

Benzhydryl 7β-[2'-(4'',5''-dihydro-2''-methyl-3''-H-1'',3'',5''-triazepin-4''-oxo-6''-yl)-2'-(E,Z)-methoximino]-3-acetoxymethyl-3-cephem-4-carboxylate

Step A

Isobutyl carbonate [2'-(4'',5''-dihydro-2''-methyl-3''-H-1'',3'',5''-triazepin-4''-oxo-6''-yl)-2'-(E,Z)-methoximino] acetate anhydride A mixture of 2'-(4'',5''-dihydro-2''-methyl-3''-H-1'',3'',5''-triazepin-4''-oxo-6''-yl)-2'-(E,Z)-methoximino acetic acid (0.5 g, 2.2 mmol) in triethylamine (0.3 ml) was stirred at 0° C. while a methylene chloride solution of isobutyl chloroformate (0.299 g, 0.282 ml) was added dropwise. The solution was stirred for 2 hours to yield isobutyl carbonate [2'-(4'',5''-dihydro-2''-methyl-3''-H-1'',3'',5''-triazepin-4''-oxo-6''-yl)-2'-(E,Z)-methoximino] acetate anhydride, which was used in situ in the following acylation (Step B).

Step B

The above methylene chloride solution of isobutyl carbonate [2'-(4'',5''-dihydro-2''-methyl-3''-H-1'',3'',5''-triazepin-4''-oxo-6''-yl)-2'-(E,Z)-methoximino] acetate anhydride was added dropwise to a methylene chloride solution (25 ml) of benzhydryl 7β-amino-3-acetoxymethyl-3-cephem-4-carboxylate (0.946 g, 2.2 mmol). The mixture was stirred overnight, then filtered, evaporated, redissolved in ethyl acetate and the ethyl acetate solution was washed with dilute acid, dilute sodium bicarbonate solution, and water, dried over magnesium sulfate, filtered and evaporated in vacuo. The residue was chromatographed over dry column silica gel, eluting with a 1:1 ethyl acetate/cyclohexane mixture, then 7:3 v:v ethyl acetate/cyclohexane mixture, and finally neat ethyl acetate. The product-containing fractions were combined, evaporated and recrystallized from acetone to give a 60:40 E:Z mixture of benzhydryl 7β-[2'-(4'',5''-dihydro-2''-methyl-3''-H-1'',3'',5''-triazepin-4''-oxo-6''-yl)-2'-(E,Z)-methoximino] -3-acetoxymethyl-3-cephem-4-carboxylate: n.m.r. (CDCl$_3$+DMSO/d$_6$) δ2.0 (s, 3, methyl of acetoxy group of the Z-isomer), 2.14 (s, 3, methyl of the acetoxymethyl group of the E-isomer and the 2''-methyl group), 2.7 (s, 3, residual acetone), 3.56 (s, 2, C-2 protons), 4.06 (s, 3, methyl group of the Z-methoxime isomer), 4.15 (s, 3, methyl group of the E-methoxime isomer), 4.76 (d, 1, J=12 Hz, C-3 methylene), 5.09 (d, 1, J=12 Hz, C-3 methylene), 5.12 (d, 1, J=4.5 Hz, C-6 proton), 5.86 (dd, 1, J=4.5, 9 Hz, C-7 proton), 6.92 (s, 1, benzhydryl methine proton), 7.32 (s, 10, benzhydryl aromatic protons), 7.92 (s, 1, C-7'' proton of the Z-isomer), 8.25 (s, 1, C-7' proton of the E-isomer), 8.57 (d, 1, J=9 Hz, C-7 amide proton of the E-isomer), 9.2 (d, 1, J=9 Hz, 7-amide proton of the Z-isomer), 10.17 (d, 1, triazepinone amide proton), 11.7 (d, 1, triazepinone amide proton).

EXAMPLE 5

7β-[2'-(4'',5''-Dihydro-2''-methyl-3''-H-1'',3'',5''-triazepin-4''-oxo-6''-yl)-2'-(E,Z)-methoximino] -3-acetoxymethyl-3-cephem-4-carboxylic acid Benzhydryl 7β-[2'-(4'',5''-dihydro-2''-methyl-3''-H-1'',3'',5''-triazepin-4''-oxo-6''-yl)-2'-(E,Z)-methoximino]-3-acetoxymethyl-3-cephem-4-carboxylate (143 mg, 0.22 mmol) was dissolved in a formic acid solution (4 ml, 97–100%) containing triethylsilane (0.04 ml, 0.25 mmol) and the solution was stirred at room temperature for 2.25 hours, placed in a freezer for 1 hour, then stirred for another 0.75 hour at room temperature. The reaction solution was then diluted with a mixture of ethyl acetate/acetonitrile, evaporated to dryness and purged with ethyl acetate/acetonitrile (2×) to give a white powder residue. The residue was triturated for 0.5 hour with diethyl ether, sonicated, filtered, washed with diethyl ether, then dried in a vacuum oven at 40° C. for 0.25 hour to give 7B-[2'-(4'',5''-dihydro-2''-methyl-3''-H-1'',3'',5''-triazepin-4''-oxo-6''-yl)-2'-(E,Z)-methoximino]-3-acetoxymethyl-3-cephem-4-carboxylic acid. The E and Z isomers were separated using high performance liquid chromatography. The conditions for this chromatography included a solvent of 8% acetonitrile, 2% acetic acid, and 90% water, the column was a LP-1 C$_{18}$ R.P. capped, with a column size of 100 ml and at a pressure of 105 psi; n.m.r. (DMSO/d$_6$) (E isomer) δ2.02 (s, 3, the methyl of the acetoxy group), 2.52 (s, 3, C-2" methyl), 3.51 (m, 2, C-2 protons), 4.02 (s, 3, methoxime methyl group), 4.72, 5.04, (ABq, 2, J=16, C-3 methylene protons), 5.12 (d, 1, J=6, C-6 proton), 5.72 (dd, 1, J=6, 12, C-7 proton), 8.35 (s, 3, C-7" proton), 8.62, 8.85 (br. s, 2, triazepinone amide protons), 9.60 (d, 1, J=12, C-7 amide proton); (Z-isomer) δ2.0 (s, 3, methyl of acetoxy group), 2.50 (s, 3, C-2" methyl group), 3.51 (m, 2, C-2 protons), 3.85 (s, 3, methyl group of methoximino function), 4.62, 5.05 (ABq, 2, J=16, C-3 methylene group protons), 5.15 (d, 1, J=6, C-6 proton), 5.75 (dd, 1, J=6, 12, C-7 proton), 7.80 (s, 1, C-7" proton), 8.61, 8.95 (br. s, 2, triazepinone ring amide protons), 9.70 (d, 1, J=12, C-7 amide proton).

I claim:
1. A compound of the formula

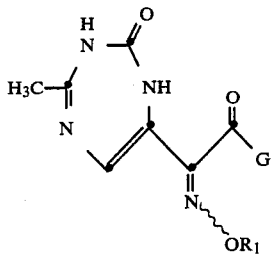

wherein:
R$_1$ is C$_1$ to C$_4$ alkyl, a carboxy-substituted alkyl, an amido-substituted alkyl, an amido-substituted cycloalkyl or carboxy-substituted cycloalkyl group represented by the formula

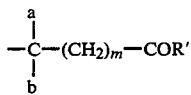

wherein m is 0 to 3, a and b when taken separately are independently hydrogen or C$_1$ or C$_3$ alkyl, or when taken together with the carbon to which they are attached form a C$_3$ to C$_7$ carbocyclic ring; R' is hydroxy, amino, C$_1$ to C$_4$ alkoxy, or —OR", where R" is 2-iodoethyl, tert-butyl, 2,2,2-trichloroethyl, 4-methoxybenzyl, 4-nitrobenzyl, diphenylmethyl, allyl, 4-methoxydiphenylmethyl, 4,4'-dimethoxydiphenylmethyl, benzyl, trialkylsilyl, 2,4,6-trimethyoxybenzyl, trityl, 4-methoxytrityl, 4,4'-dimethoxytrityl, or 4,4',4"-trimethoxytrityl; G is chloro, bromo, hydroxy, C$_1$ to C$_4$ alkoxy, phenoxy, or a group of the formula

wherein J is p-nitrophenyl, 2,4-dinitrophenyl, pentachlorophenyl, a group of the formula

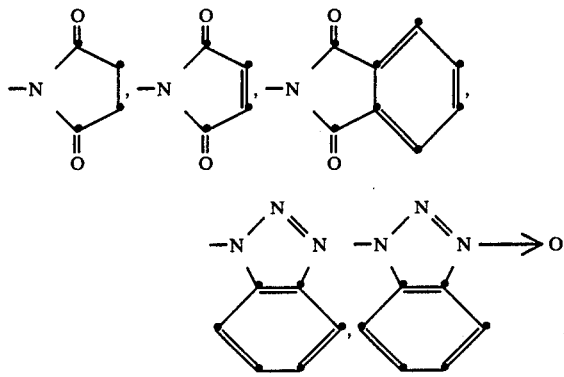

methoxycarbonyl, iso-butoxycarbonyl, pivaloyl, or trichloroacetyl; or a group of the formula

wherein M$^⊕$ is lithium, sodium, potassium, ammonium, dibenzyl ammonium, benzylammonium, phenylethylbenzylammonium, 2-hydroxyethylammonium, or dicyclohexylammonium.

2. A compound of claim 1, wherein R$_1$ is C$_1$ to C$_4$ alkyl.
3. A compound of claim 2, wherein R$_1$ is methyl.
4. A compound of claim 3, wherein G is ethoxy.
5. A compound of claim 3, wherein G is a group of the formula

6. A compound of claim 3, wherein G is hydroxy.
7. A compound of claim 3, wherein G is isobutylcarbonate.

* * * * *